United States Patent [19]

Kirsch et al.

[11] Patent Number: 5,529,993
[45] Date of Patent: Jun. 25, 1996

[54] 14α, 17α-ETHANO-16α-HYDROXY-ESTRATRIENES

[75] Inventors: Gerald Kirsch; Günter Neef; Henry Laurent; Rudolf Wiechert, all of Berlin, Germany; James Bull, Pretoria, South Africa; Peter Esperling, Berlin, Germany; Walter Elger, Berlin, Germany; Sybille Beier, Berlin, Germany

[73] Assignee: Schering Aktiengesellschaft, Berlin, Germany

[21] Appl. No.: 619,947

[22] Filed: Nov. 29, 1990

[30] Foreign Application Priority Data

Nov. 29, 1989 [DE] Germany .......................... 39 39 894.3
Nov. 29, 1989 [DE] Germany .......................... 39 39 893.5
Oct. 22, 1990 [DE] Germany .......................... 40 33 871.1

[51] Int. Cl.⁶ .............................. C07J 1/00; A61K 31/565
[52] U.S. Cl. .......................... 514/182; 514/843; 514/935; 552/617
[58] Field of Search ............................. 552/617; 514/182, 514/843, 935

[56] References Cited

U.S. PATENT DOCUMENTS 4,789,671 12/1988 Bull et al. ................................ 514/182

OTHER PUBLICATIONS

Pharmazeutische Chemie; Stroder et al., 1982; pp. 569–577.
"Drug Research" 27, 2A, 296–318 (1977).

*Primary Examiner*—Kimberly J. Prior
*Attorney, Agent, or Firm*—Millen, White, Zelano, & Branigan

[57] ABSTRACT

A 14α,17α-bridged estratriene of formula I

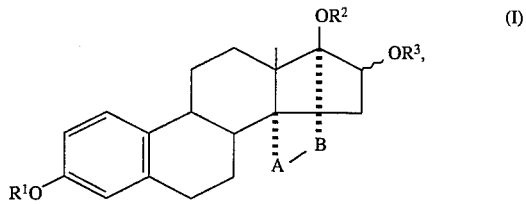

wherein (a) $OR^3$ is in α-position $R^1$, $R^2$ and $R^3$, each independently are (i) hydrogen, (ii)

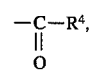

in which $R^4$ is an organic radical with up to 11 carbon atoms or (iii) —$(CH_2)_n$COOH wherein n= 1–4, or (iv) $R^1$ is a benzyl, $C_1$–$C_8$ alkyl or $C_3$–$C_5$ cycloalkyl, or (b) $OR^3$ is in β-position $R^1$, $R^2$ and $R^3$, each independently are (i) hydrogen, (ii) an acyl group with 1 to 12 carbon atoms or (iii) $R^1$ is $C_1$–$C_8$ alkyl, and in both (a) and (b) A—B is an etheno or ethano bridge.

19 Claims, 1 Drawing Sheet

14α, 17α-ETHANO-16α-HYDROXY-ESTRATRIENES

SUMMARY OF THE INVENTION

This invention relates to 14α,17α-bridged estratrienes of general formula I

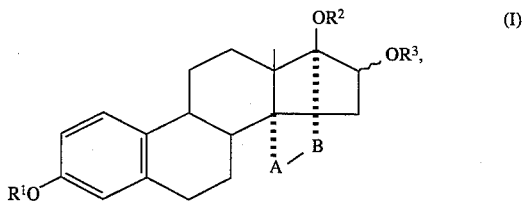

in which if OR³ is in α-position

R¹, R² and R³, independent of one another, stand for a hydrogen atom, an acyl group

in which R⁴ is an organic radical with up to 11 carbon atoms or the radical —(CH₂)ₙCOOH with n= 1–4 is a carboxylic acid, as well as, further, R¹ stands for a benzyl radical, C₁–C₈ alkyl radical or C₃–C₅ cycloalkyl radical and if OR³ is in β-position R¹, R² and R³, independent of one another stand for a hydrogen atom, an acyl group with 1 to 12 carbon atoms and R¹ in addition stands for a C₁–C₈ alkyl radical and in both cases, A—B means an etheno or ethano bridge, a process for their production, pharmaceutical preparations, which contain these compounds as well as their use for the production of pharmaceutical agents.

As acyl groups R¹, R² and R³, radicals of organic carboxylic acids with 1–12 carbon atoms are suitable. They are derived from aliphatic, cycloaliphatic, aliphatic-cycloaliphatic, cycloaliphatic-aliphatic and aromatic monocarboxylic acids with 1 to 12 carbon atoms. The number of carbon atoms in the ring varies from 3 to 7. One or two unsaturations may be present in the aliphatic or cycloaliphatic moieties. The acyl groups of acetic, propionic, butyric, isobutyric, pivalic, caproic, acrylic, crotonic, heptanoic, caprylic, pelargonic, decanoic, undecanoic, dodecanoic, 3-cyclopentylpropionic and benzoic acid are preferred as radicals R¹, R² and R³.

Acyl radicals R¹, R² and R³ especially are to be derived from such carboxylic acids, which exhibit 2 to 8 carbon atoms.

Acyl groups R¹, R² and R³ can also be derived from dicarboxylic acids with up to 6 carbon atoms; here, especially the succinic acid is meant.

If R¹ is an alkyl radical, above all the methyl radical is meant; also, the ethyl, propyl and isopropyl radicals are especially important. As a cycloalkyl radical, the cyclopentyl radical is preferred for R¹.

The organic radical R⁴ preferably is alkyl, alkenyl, dialkenyl, cycloalkyl, cycloalkenyl, alkyl-cycloalkyl or cycloalkyl-alkyl, in which the cycloalkyl portions have 3–7 carbon atoms, or $C_{5-11}$-aromatic.

Within the scope of this invention, the following compounds are to be emphasized:

3-benzyloxy-14α,17α-ethano-1,3,5(10)-estratriene-16α,17β-diol;
14α,17α-ethano-1,3,5(10)-estratriene-3,16α,17β-triol;
14α,17α-ethano-3-methoxy-1,3,5(10)-estratriene-16α,17β-diol;
16α,17β-diacetoxy-14α,17α-ethano-3-methoxy-1,3,5,(10)-estratriene;
3,16α,17β-triacetoxy-14α,17α-ethano-1,3,5(10)-estratriene.
14α,17α-etheno-1,3,5(10)-estratriene-3,16β,17β-triol
14α,17α-etheno-3-methoxy-1,3,5(10)-estratriene-16β,17β-diol
14α,17α-etheno-3-methoxy-1,3,5(10)-estratriene-16α,17β-diol
14α,17α-ethano-1,3,5(10)-estratriene-3,16β,17β-triol
3-acetoxy-14α,17α-etheno-1,3,5(10)-estratriene-16β,17β-diol
16β-diacetoxy-14α,17α-etheno-1,3,5(10)-estratrien-17β-ol
4α,17α-etheno-1,3,5(10)-estratriene-3,16β,17β-triol-triacetate
16β,17β-diacetoxy-14α,17α-etheno-1,3,5(10)-estratrien-3-ol
14α,17α-etheno-1,3,5(10)-estratriene-3,16β,17β-triol
14α,17α-etheno-1,3,5(10)-estratriene-3,16α,17β-triol
3,16β-diacetoxy-14α,17α-ethano-1,3,5(10)-estratrien-17β-ol
14α,17α-ethano-1,3,5(10)-estratriene-3,16β,17β-triol-triacetate
3-acetoxy-14α,17α-ethano-1,3,5(10)-estratriene-16β,17β-diol
14α,17α-ethano-1,3,5(10)-estratriene-3,16β,17β-triol
14α,17α-ethano-1,3,5(10)-estratriene-3,16α,17β-triol.

14α,17α-etheno-bridged steroids are described in J. Chem. Commun., 1986, 451–453 and 14α,17α-etheno-bridged and 14α,17α-ethano-bridged steroids in international patent application PCT/DE87/00361 as the compounds coming closest to the compounds of the general formula I. In the Allen-Doisy test for estrogenic effect, these compounds are more strongly estrogenically effective than ethinylestradiol.

The compounds of the general formula I according to the invention are distinguished from the known 14α,17α-ethano-bridged estratrienes by the additional presence of a free or esterified α-position hydroxy group on the 16 carbon atom.

On the other hand, the naturally occurring 16α-estriol (1,3,5(10)-estratriene-3,16α,17β-triol) is known as an oral estrogenically effective steroid with 3 hydroxy functions (E. Schroeder, C. Rufer, R. Schmiechen, Pharmazeutische Chemie [Pharmaceutical Chemistry], Georg Thieme Verlag Stuttgart, New York, 1982, p. 571 ff.)

Just like said compounds belonging to the prior art, the compounds according to the invention are distinguished by an extraordinarily strongly estrogenic effectiveness.

The compounds of the general formula I are more strongly effective than estriol (table 1, column 4) after subcutaneous administration in the Allen-Doisy test.

In the Allen-Doisy test, an evaluation of vaginal smears in ovariectomized rats is performed on days 1–5 after the single administration (on d1) of the test substance. The following cycle stages are distinguished:

1= diestrus (leukocytes and nucleated epithelial cells),

2= proestrus (nucleated epithelial cells),

3= estrus (denucleated horny plaques),

4= metestrus (denucleated horny plaques, leukocytes, epithelial cells).

After oral or subcutaneous administration, estrogenically effective substances result in the proliferation of vaginal epithelium and in the hornification of surface cell conditions. A threshold value of an estrogen is considered as the amount at which 50% of the animals reach stage 3.

But unlike estriol the compounds according to the invention are also are strongly estrogenically effective after oral administration since the catabolism of the 17-OH group is blocked by the tertiary 17-carbon atom.

FIG. 1 shows the extraordinarily clear superiority of 14α,17α-ethano-estra-1,3,5(10)-triene-3,16α,17β-triol in comparison with 14α,17α-ethano-estra-1,3,5(10)-triene-3, 17β-diol (as well as in comparison with estradiol and ethinylestradiol) also after peroral administration.

This clear effect is to be considered as especially surprising. The transition of estradiol to the corresponding 14α, 17α-bridged derivative 14α,17α-ethano-estra- 1,3,5(10)-triene-3,17β-diol has hardly any influence, relative to the estrogeneity, in subcutaneous administration; consequently, a comparable estrogenic effect with estriol was to be expected for the 14α,17α-ethano-estra- 1,3,5(10)-triene-3, 16α,17β-triol according to the invention.

The active ingredient concentration in the pharmaceutical compositions is dependent on the form of administration and the field of use. Thus, for example, for the treatment of estrogen deficiency symptoms, capsules or tablets can contain 0.001 to 0.05 mg of active ingredient, oily solutions for intramuscular injection per 1 ml approximately 0.01 to 0.1 mg of active ingredient and vaginal ointments about 0.1 to 10 mg per 100 ml of ointment. For contraception in the female, the estrogens according to the invention are preferably used in combination with gestagens. Tablets or coated tablets for daily intake contain preferably 0.003 to 0.05 mg of the estrogen according to the invention and 0.05 to 0.5 mg of a gestagen. In principle, any gestagen known to one of ordinary skill in the art may be used in combination with the compounds of the invention. Preferred gestagens include medroxyprogesteron- and -acetate, nomegestrolaetate, megestrol-acetate, desogestrel, dihydrospirorenon (6β,7α; 15β,16β-dimethylen-3-oxo-4 -androsten-[17(β-1')-spiro-5']-perhydrofuran-2'-on) levonorgestrel, gestoden, norethisteron and -acetate, cyproteronacetate, chlormadinonacetate, ethinodioldiacetate and lynestrenol.

The compounds according to the invention can be used in the case of estrogen deficiency symptoms of the female, such as, for example, amenorrhea, dysmenorrhea, sterility, endometritis, colpitis and menopausal symptoms and for the prevention or treatment of osteoporosis. Further, the compounds can be used as estrogenic components in hormonal contraceptives (single-phase and multiphase and multistage

TABLE 1

Vaginal smear test according to Allen and Doisy in the s.c. administration.
Injection: d1 (1X): Vaginal smear d1–d5 (1X daily).
Autopsy d5, n = 6 animals/groups: control n = 12 animals or n = 6 animals

| (1) Substance | (2) Dose in μg | (3) Body weight (g) | | | | (4) Vaginal smear n. positive/ n. treatment | Uterus weight mg/100 g body weight | | | |
|---|---|---|---|---|---|---|---|---|---|---|
| | | d1 | | d5 | | | (moist) | | (dry) | |
| | | X | Sx | X | Sx | | X | Sx | X | Sx |
| 14α, 17α-ethano-1,3,5(10)-estra-triene-3, 16α, 17β-triol | 3.0 | 215 | 5.6 | 220 | 8.1 | 6/6 | 79.7 | 15.9 | 13.8 | 1.7 |
| | 1.0 | 214 | 9.4 | 221 | 10.2 | 6/6 | 64.6 | 7.4 | 12.0 | 1.9 |
| Estriol = estriol | 3.0 | 215 | 7.3 | 227 | 12.8 | 4/6 | 39.1 | 5.4 | 7.6 | 0.7 |
| | 1.0 | 225 | 12.2 | 228 | 10.7 | 1/6 | 43.0 | 11.1 | 8.3 | 1.7 |
| Control benzyl benzoate + castor oil (1 + 4)/0.5 ml | — | 213 | 4.8 | 231 | 7.1 | 0/12 | 36.2 | 7.7 | 7.3 | 1.6 |

Thus, the invention also relates to compounds of general formula I for use in the treatment of estrogen deficiency symptoms and for birth control in female mammals, preferably humans.

The compounds according to the invention can be formulated and used in the same way as ethinylestradiol, which is the estrogen most used. They are processed according to methods known in the art into the usual pharmaceutical agent forms with the additives, vehicles and/or taste corrigents usual in galenic pharmacy. For oral administration, tablets, coated tablets, capsules, pills, suspensions or solutions are especially suitable. For parenteral administration, oily solutions, such as, for example, sesame oil or castor oil solutions, are especially suitable, which can optionally contain in addition another diluent, such as, for example, benzyl benzoate or benzyl alcohol.

preparations). Further, they are suitable in connection with other active ingredients for use in hormone-carrying intrauterine pessaries, implantable active ingredient vehicles as well as in transdermal administration systems.

The new compounds of general formula I

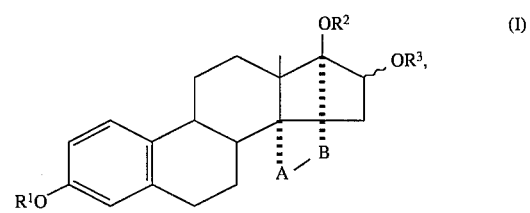

in which if $OR^3$ is in α-position $R^1$, $R^2$ and $R^3$, independent of one another, stand for a hydrogen atom, an acyl group

in which $R^4$ is an organic radical with up to 11 carbon atoms or radical $-(CH_2)_n COOH$ with n= 1–4 is a carboxylic acid, as well as, further, $R^1$ stands for a benzyl radical, $C_1$–$C_8$ alkyl radical or $C_3$–$C_5$-cycloalkyl radical and if $OR^3$ is in β-position $R^1$, $R^2$ and $R^3$, independent of one another, stand for a hydrogen atom, an acyl group with 1 to 12 carbon atoms and $R^1$ in addition stands for a $C_1$–$C_8$ alkyl radical and in both cases, A—B means an etheno- or ethano-bridge, are produced, by A) a compound of the general formula II

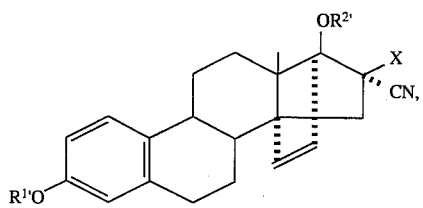

in which $R^{1'}$ stands for an acetyl or methyl radical, $R^{2'}$ stands for an acetyl radical and X stands for an acetoxy radical or a chlorine atom, a) if $R^{1'}$ stands for an acetyl radical, being reacted either with potassium tri-sec-butyl borohydride or with a base for the compound of formula III

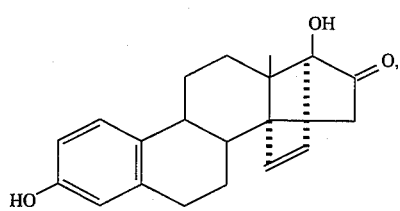

and III then either being further reduced with lithium aluminum hydride to a mixture of the 16α-hydroxy and 16β-hydroxy compounds of formulas IVa and IVb

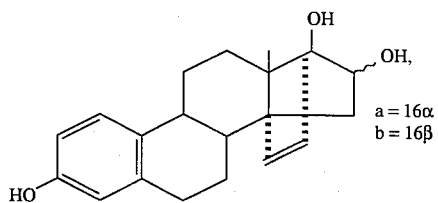

or III then to compound IIIa

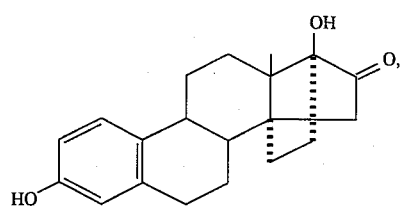

being catalytically hydrogenated and IIIa being reduced with lithium alanate to a mixture of compounds VIIa and VIIb

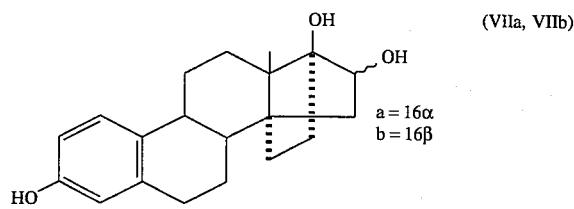

and VIIa/VIIb optionally being further processed as described below or II being reacted with sodium borohydride to the compound of formula IVb

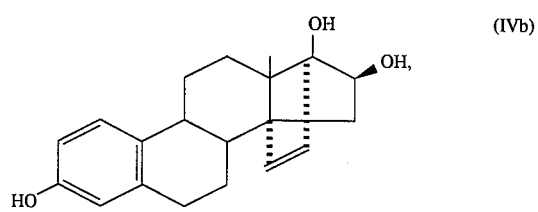

or b) if $R^{1'}$ stands for a methyl radical II being saponified to the compound of formula V

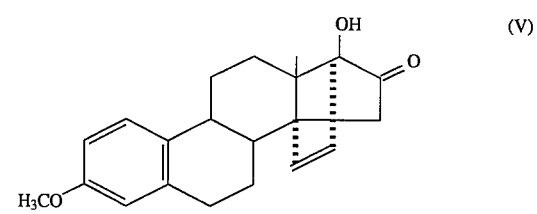

and then being reduced with lithium alanate to a mixture of 16α-hydroxy compounds and 16β-hydroxy compounds of formula VIa and VIb

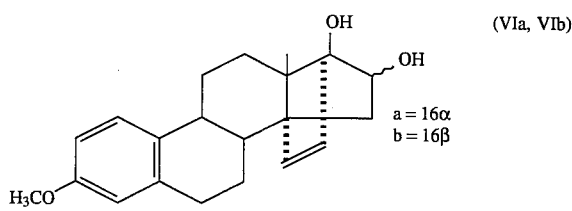

and then optionally the 3-methyl ether being cleaved with the formation of compounds IVa and IVb and optionally either c) after step a) or b) first the compound of formula IVb or the mixture of compounds of formulas IVa and IVb either being catalytically hydrogenated to the compound of formula VIIb or to the mixture of compounds of formulas VIIa and VIIb and then optionally the compound of formula VIIb or the mixture of formulas VIIa and VIIb being partially or completely esterified or optionally the free 3-hydroxy group being etherified and/or the other free hydroxy groups being esterified or else optionally d) after step a) or b) first the compound of formula IVb or the mixture of the compounds of formulas IVa and IVb selectively in 3 position with the formation of the compound of formula VIIIb or the mixture of the compounds of formulas VIIIa and VIIIb

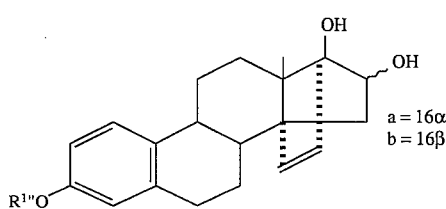

(VIIIa, VIIIb)

a = 16α
b = 16β in which R$^{1''}$ is an acyl radical with 1 to 12 carbon atoms, being esterified and then optionally either the compound of formula VIIIb or the mixture of compounds VIIIa and VIIIb either to the compound of formula IXb or the mixture of compounds IXa and IXb

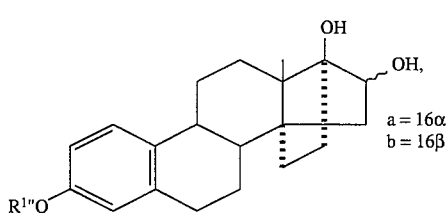

(IXa, IXb)

a = 16α
b = 16β in which R$^{1''}$ is an acyl radical with 1 to 12 carbon atoms, being catalytically hydrogenated and optionally IXb or IXa/IXb being partially or completely esterified or optionally the free 3-hydroxy group being etherified and/or the other free hydroxy groups being esterified or VIIIb or VIIIa/VIIIb being optionally successively further esterified and optionally the 3-acyl group being selectively saponified and/or the 3-hydroxy group being optionally etherified, or B) for the production of compounds, in which OR$^3$ is only in α-position, a compound of general formula XIIa

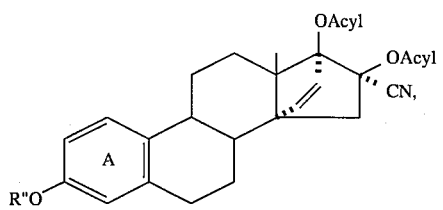

(XIIa)

in which

R' means an acyl or methyl group, or a compound of the general formula XIIb

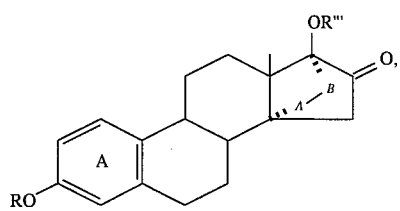

(XIIb)

in which R means a hydrogen atom or a methyl group, A—B means a C—C single bond or a C—C double bond and R''' means a hydrogen atom or an acyl group with 1 to 12 carbon atoms, with an alkali metal in liquid ammonia with obtaining the aromatic system in an A-ring and optionally the double bond in A—B being reduced and the 14α,17α-etheno bridge optionally being hydrogenated and optionally the substituents being functionalized in 3, 16 and/or 17 position as already indicated above or C) for the production of compounds, in which OR$^3$ is only in α-position and A—B stands only for an ethano-bridge, a compound of the general formula XXII

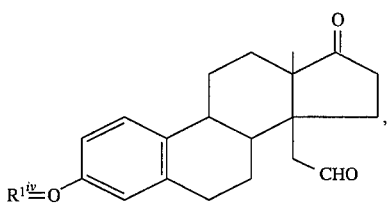

(XXII)

in which R$^{1IV}$ stands for a benzyl or methyl radical, being cyclized to a compound of the general formula I'

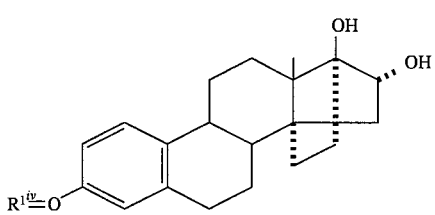

(I')

and then optionally the 3-benzyl- or 3-methyl ether being cleaved and free hydroxy groups then being partially or completely esterified, or optionally the free 3-hydroxy group being etherified and/or the other free hydroxy groups being esterified or optionally after the cyclization first the free 16α- and 17β-hydroxy group being esterified and then optionally the 3-benzyl or 3-methyl ether being cleaved and optionally the free 3-hydroxy group being etherified or esterified again.

For process variant A)

The production of the initial products of general formula II takes place by a reaction of 3-acetoxy- or 3-methoxy-1,3,5(10),14,16-estrapentaen-17-ol acetate (G. H. Rasmusson et al., Steroids 22, 107, (1973)) with α-acetoxyacrylonitrile or α-chloroacrylonitrile. The two last-mentioned compounds act as ketene equivalents for a [4+2]-cycloaddition with the diene system in the D-ring of the steroidal initial compounds. Previously, only their reaction with cyclopentadiene was known ("Ketene Equivalents," Synthesis 1977, pp 289–296). These initial products of general formula II therefore also belong to the object of the invention.

The production of the compounds of general formula IVa and IVb from the initial compounds of general formula II (R$^{1'}$= acetyl) takes place by the 16-ketone of formula III. With saponification of II with a usual base for saponification reactions or with a reduction of II with a complex hydride such as K-Selectide $^{(R)}$ (potassium tri-sec-butyl borohydride), the reaction remains in the stage of 16-ketone III.

The 16-keto group in III can then be further reduced by using another sterically less exacting complex hydride to the hydroxy function. Examples for this purpose are sodium borohydride or lithium aluminum hydride, which represents the sterically least exacting complex hydride. Reduction of initial compounds II (R$^{1'}$ = acetyl) with one of the two last-mentioned reducing agents likewise leads to a 16 -hydroxy function. Depending on the size (steric demand) of the complex hydride, the 16-keto group is exclusively converted to a 16β-hydroxy function or to a mixture of the 16α and 16β-hydroxy isomers. The 16α-hydroxy function can be established only with a sterically demand-free complex hydride, since in this case, its attack has to take place from the double bond side (in the direction of the 14α,17α-etheno bridge).

Under the indicated conditions, acetoxy groups in 3- and 17-position are reductively cosaponified at the same time. Depending on the desired end product, starting from IVb/IVa, further reactions optionally can follow after the previous separation of the two isomers.

The double bond of the 14α,17α-etheno bridge can easily be catalytically hydrogenated (IVa/IVb→VIIa/VIIb) and the hydroxy groups of the ethano compound or compounds VIIa/VIIb then can be successively esterified. Also, IVa/IVb first can be partially esterified and then the double bond of the 14α,17α-etheno bridge can be catalytically hydrogenated, by which finally partially or completely esterified 14α,17α-ethano compounds are produced.

For esterification of free hydroxy groups, known processes are used (reaction of the free OH compound with the corresponding carboxylic acid chloride or anhydride.) By taking into consideration the different reactivities of the free 3-, 16- and 17-hydroxy groups, the partially esterified compounds as well as the compounds esterified by successive esterification with different esterification reagents—which exhibit different acyl groups $R^1$ and/or $R^2$ and/or $R^3$—can be produced.

By selective saponification of compounds of general formula I, which are esterified also in 16- and/or 17-position in addition to 3-position, 3-hydroxy compounds, which are esterified in 16- and/or 17-position, are produced.

Thus not only the acetoxy compounds described in the examples can be produced from trihydroxy compounds IVa/IVb and VIIa/VIIb but also higher esters, such as propionates, butyrates, valerates, etc., which, e.g., can be of interest for formulations to be used topically.

Another variant according to the invention consists in producing the 16-keto compound III as described and catalytically hydrogenating it to the corresponding 14α,17α-ethano compound and then reducing the resulting 14α,17α-ethano-16-keto compound, and by using lithium aluminum hydride as a reducing agent, again both 16-hydroxy isomers VIIa/VIIb are obtainable, which can be separated and—as already indicated—can be further processed.

The access to the compounds according to the invention is also possible starting from a compound of general formula II, in which $R^{1'}$ stands for a methyl group, by saponification with a base, for example with potassium hydroxide, and first the 14α,17α-etheno-bridged 3-methoxy- 16-ketone is formed. The latter can be further reduced; also with lithium aluminum hydride a mixture of 16α-hydroxy and 16β-hydroxy compound VIa/VIb is achieved; optionally, this mixture can be separated. Unlike using a 3-acetoxy compound as a starting material, the 3-methoxy compound remains intact in the saponification and reduction so that if $R^1$ is finally to be a group other than the methyl radical, the 3-methyl ether has to be cleaved. Conventional processes of ether cleavage are used for this purpose, such as, for example, the reaction with diisobutyl aluminum hydride. The products of formulas IVa/IVb obtained can, as described above, be further reacted.

The scope of this invention also extends to the intermediate compounds of general formulas III, IIIa and V.

For process variant B)

The Diels-Alder compounds IIa with alkali metals in liquid ammonia stereoselectively produce the 3,16α,17β-triols I', which can then also be hydrogenated to the ethano compounds I". The reaction described here proceeds quite obviously by radicals, and thermodynamically stable products are formed.

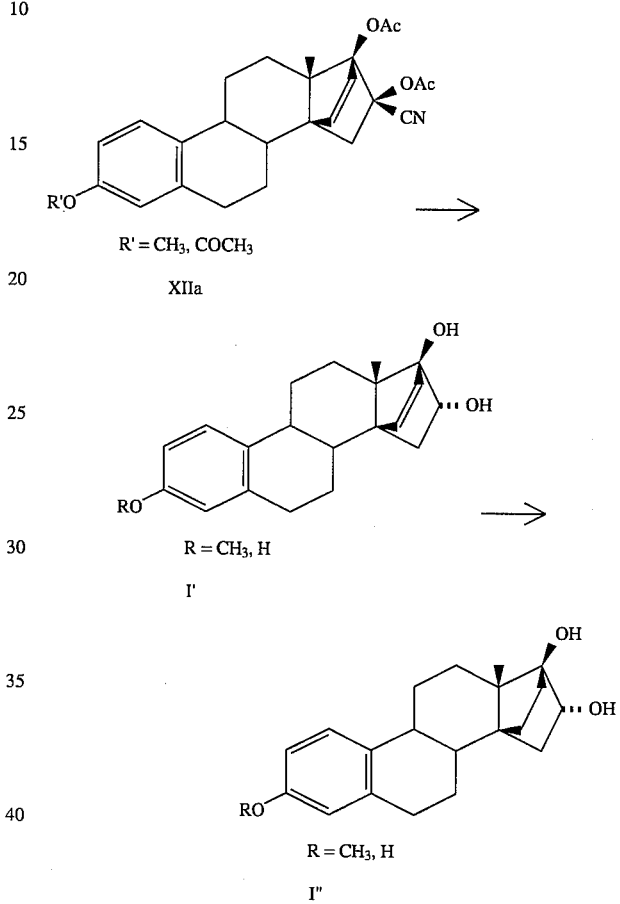

According to the process described above, the 16-ketones XIIb' and XIIb" can also be reduced radically stereoselectively to 3,16α,17β-estriols I' or I" with sodium in ammonia. Optionally present ester groups, e.g. in tertiary 17-position, are saponified under the reaction conditions.

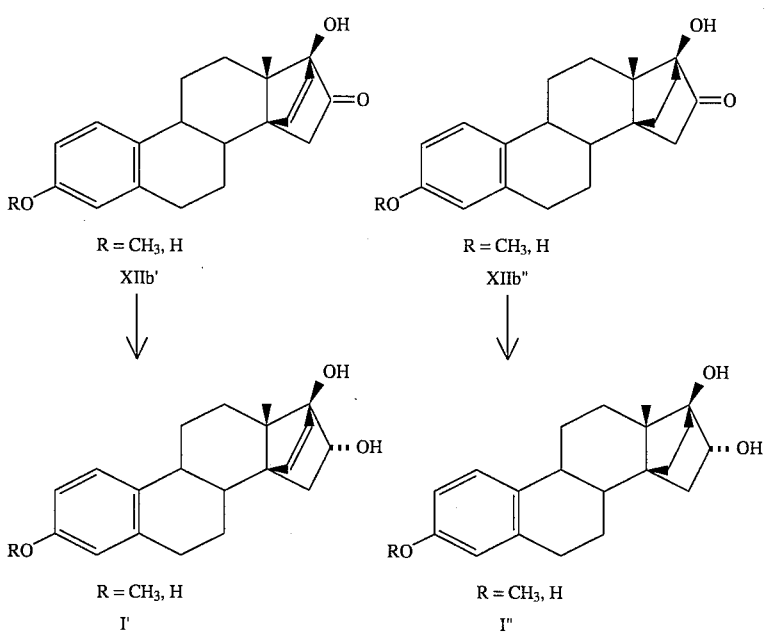

Reduction B) according to the invention is preferably performed with sodium as an alkali metal.

The reaction temperature in this connection is preferably kept below −60° C., for example with cooling with dry ice (−78° C.).

Under the indicated reaction conditions, the aromatic system of A-rings is obtained.

For process variant C)

The cyclization of the compounds of general formula II takes place by a radical anion as a reactive species; this is formed from the aldehyde function according to the invention by reduction with a mixture of TiCl$_4$/Zn powder. But for the reductive coupling, the use of the systems Mg/Hg-TiCl$_4$, Mg-TiCl$_3$ or Al/Hg is also possible.

The cleavage of the benzyl ether takes place hydrogenolytically according to the invention. The 3-methoxy group can be cleaved by reaction with Lewis acids; for example, a mixture of sodium iodide/trimethylchlorosilane can be used for this purpose. This cleavage can take place directly after the cyclization, which results in the compound of the general formula I, in which $R^1$, $R^2$ and $R^3$ are each a hydrogen atom.

But the 16- and 17-hydroxy groups can first be esterified also in a compound of the general formula I' and then the ether function can be cleaved in 3-position and the 3-hydroxy group formed then optionally can be again esterified ($R^1$ is not equal to $C_6H_5CH_2$— or —$CH_3$) or etherified.

For esterification of free hydroxy groups, known processes are used (reaction of the free OH compound with the corresponding carboxylic acid chloride or anhydride). By considering the different reactivities of the free 3-, 16- and 17-hydroxy groups, the partially esterified compounds as well as the compounds esterified by successive esterification with different esterification reagents—which exhibit different acyl groups $R^1$ and/or $R^2$ and/or $R^3$—can be produced.

By selective saponification of the compounds of general formula I, which are esterified in 3-position and also in 16- and/or 17-position, 3-hydroxy compounds, which are esterified in 16- and/or 17-position, are produced.

The range of this invention also extends to the compounds of general formula XXII

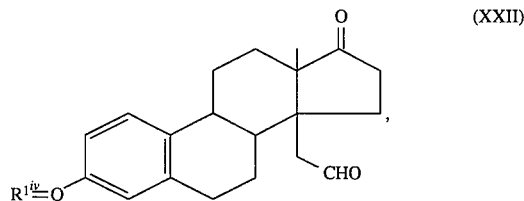

in which $R^{1IV}$ stands for a methyl or benzyl radical; they are used as initial products for the cyclization. In this case, if a benzyloxy radical is in 3-position, its ether bond can optionally be easily cleaved hydrogenolytically after the cyclization.

BRIEF DESCRIPTION OF THE DRAWING

FIG. 1 shows the uterotropic effect of 14α,17α-ethano-estra-1,3,5(10)-triene- 3,16α,17β-triol and 14α,17α-ethano-estra-1,3,5(10)-triene- 3,17β-diol in rats.

Figure 1:
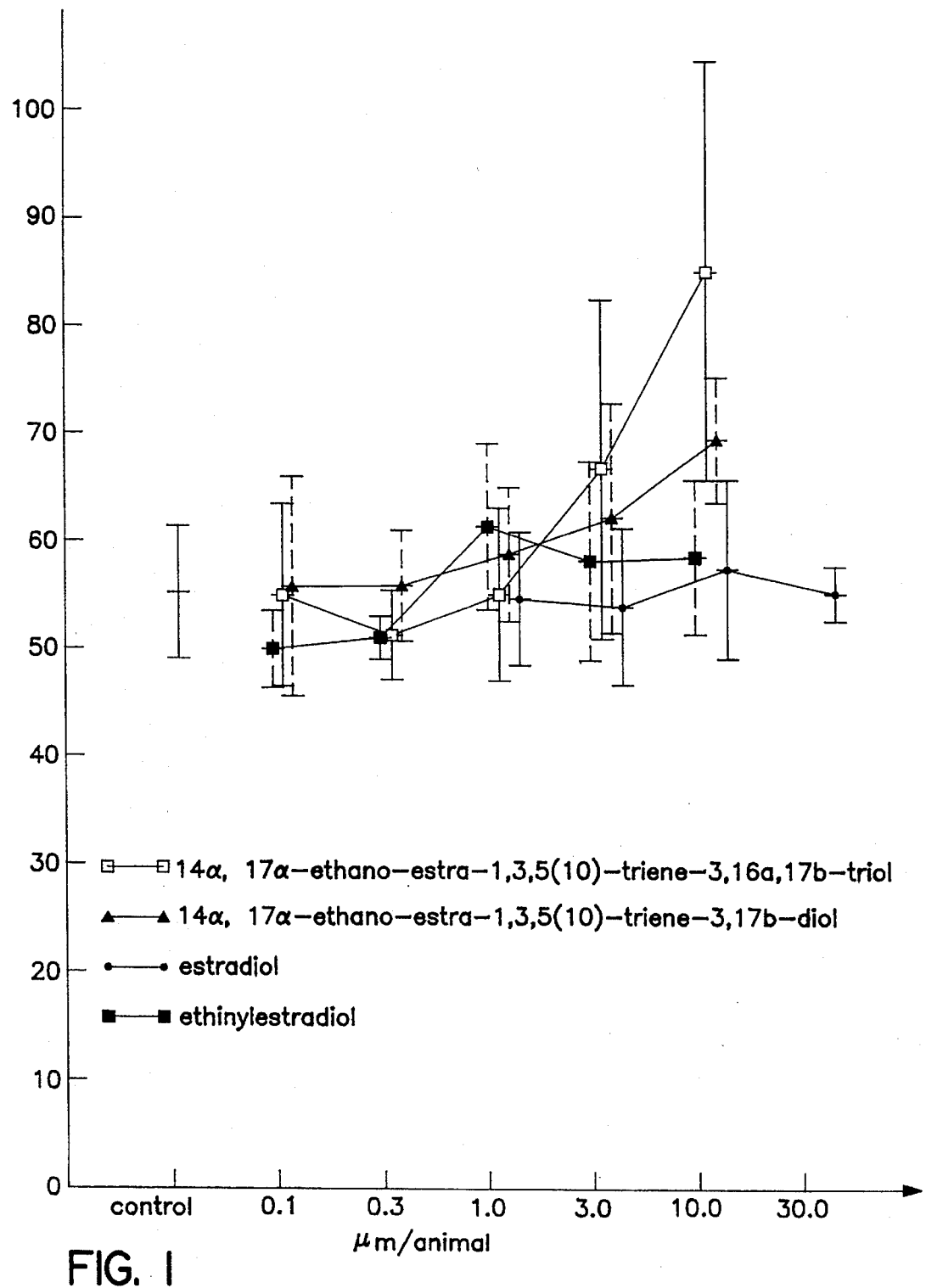
FIG. 1 shows the superiority of a compound in accordance with the invention with a nonconforming compound and with conventional estradiol and ethinylestradiol after peroral administration. Specifically.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding applications Federal Republic of Germany 39 39 894.3, filed Nov. 29, 1989; Federal Republic of Germany 39 39 893.5, filed Nov. 29, 1989; and Federal Republic of Germany 40 33 871.1, filed Oct. 22, 1990, are hereby incorporated by reference.

EXAMPLES

Example 1

3,16β,17β-Triacetoxy-14α,17α-etheno-1,3,5(10)-estratriene- 16α-carbonitrile

A solution of 1.0 g of 1,3,5(10),14,16-estrapentaene-3,17-diol diacetate in 5 ml of dry benzene is mixed with 5 ml of 1-cyanovinyl acetate and 10 mg of hydroquinone and heated for 3 days in a closed tube to 140° C. The partially resinified reaction mixture is treated with boiling dichloromethane. After the decanting and evaporation of the solvent, 1.61 g of a crystalline residue remains which is chromatographed on 400 g of silica gel. It is eluted with a hexane-ethyl acetate gradient (0–50% ethyl acetate) and 1.30 g is obtained which recrystallized from dichloromethane-diisopropyl ether yields 882 mg of 3,16β,17β-triacetoxy- 14α,17α-etheno-1,3,5(10)-estratriene-16α-carbonitrile. Melting point: 164° C.

Example 2

16β,17β-Diacetoxy-14α,17α-etheno-3-methoxy-1,3,5(10)-estratriene- 16α-carbonitrile A solution of 200 mg of 3-methoxy-1,3,5(10),14,16 -estrapentaen-17-ol acetate in 2 ml of benzene is mixed with 0.26 ml of 1-cyanovinyl acetate and heated in a closed tube for 63 hours to 145° C. The reaction mixture is filtered on Celite$^{(R)}$ and concentrated by evaporation in a vacuum. The residue of 338 mg, chromatographed as an eluent on 20 g of silica gel with ethyl acetate-toluene (5:95), yields 189 mg of 16β,17β-diacetoxy-14α,17α-etheno-3-methoxy-1,3,5(10)-estratriene- 16α-carbonitrile. Melting point: 145° C.

Example 3

14α,17α-Etheno-1,3,5(10)-estratriene-3,16β,17β-triol

A solution of 240 mg of 3,16β,17β-triacetoxy-14α,17α-etheno-1,3,5(10)-estratriene-16α-carbonitrile in 6 ml of anhydrous ethanol is mixed with 600 mg of sodium borohydride in 13 ml of ethanol and stirred for 15 hours at room temperature. The reaction mixture is diluted with ethyl acetate, the solution is washed with water, dried on sodium sulfate and concentrated by evaporation in a vacuum. The residue, 190 mg, is chromatographed on 150 g of silica gel with a dichloromethane-methanol mixture (95:5). 140 mg of an oil is eluted. After the crystallization from dichloromethane-hexane, 83 mg of 14α,17α-etheno-1,3,5(10)-estratrien- 3,16β,17β-triol is obtained. Melting point: 199° C.

Example 4

3-Methoxy-14α,17α-etheno-17β-hydroxy-1,3,5(10)-estratrien- 16-one

A solution of 48 mg of 16β,17β-diacetoxy-14α,17α-etheno- 3-methoxy-1,3,5(10)-estratriene-16α-carbonitrile in a mixture of 1.0 ml of dimethyl sulfoxide and 1.0 ml of tetrahydrofuran is mixed at 0° C. with 0.07 ml of 2N potassium hydroxide solution. After 18 hours, another 0.07 ml of 2N potassium hydroxide solution is added, after 22 hours, the reaction is completed. The working up yields 32 mg of a residue which is chromatographed on silica gel. After the recrystallization from chloroform-methanol, 15 mg of 3-methoxy-14α,17α-etheno-17β-hydroxy-1,3,5(10)-estratrien- 16-one is obtained. Melting point: 159° C.

Example 5

14α,17α-Etheno-3-methoxy-1,3,5(10)-estratriene-16β,17β-diol and 14α,17α-etheno-3-methoxy-1,3,5(10)-estratriene-16α,17β-diol A solution of 170 mg of 3-methoxy-14α,17α-etheno-17β-hydroxy-1,3,5(10)-estratrien-16-one in 10 ml of tetrahydrofuran is mixed under nitrogen at 0° C. with 60 mg of lithium aluminum hydride. After 1.5 hours, the reaction is completed by adding aqueous ammonium hydrochloride solution. Then, it is extracted with ethyl acetate, the extract is washed with water, dried with magnesium sulfate and concentrated by evaporation in a vacuum. 160 mg of a crystalline product remains, which, chromatographed on 16 g of silica gel with ethyl acetate-hexane (3:2) as an eluent, yields 123 mg of 14α,17α-etheno-3-methoxy-1,3,5(10)-estratriene- 16β,17β-diol, melting point: 162° C. (from chloroform-methanol), as well as 32 mg of 14α,17α-etheno-3 -methoxy-1,3,5(10)-estratriene-16α,17β-diol, melting point: 195° C. (from methanol-toluene).

Example 6

14α,17α-Ethano-1,3,5(10)-estratriene-3,16β-17β-triol

A solution of 110 mg of 14α,17α-etheno-1,3,5(10)-estratriene- 3,16β,17β-triol in a mixture of 6 ml of ethanol and 1.5 ml of tetrahydrofuran is mixed with 20 mg of palladium-carbon (10% Pd) and hydrogenated under normal pressure. After absorption of 10.5 ml of hydrogen (calculated 8.7 ml), the catalyst is filtered off within 30 minutes. The filtrate is concentrated by evaporation in a vacuum and the residue is recrystallized from a methanol-diisopropyl ether mixture. Yield: 105 mg of 14α,17α-ethano-1,3,5(10)-estratriene-3, 16β,17β-triol. Melting point: 230° C.

Example 7

3-Acetoxy-14α,17α-etheno-1,3,5(10)-estratriene-16β,17β-diol and 3,16β-diacetoxy-14α,17α-etheno-1,3,5(10)-estratrien- 17β-ol A solution of 130 mg of 14α,17α-etheno-1,3,5(10)-estratriene- 3,16β,17β-triol in a mixture of 1.4 ml of pyridine and 0.6 ml of acetic anhydride is allowed to stand for 3 hours at room temperature. The reaction product is precipitated by adding water and taken up in dichloromethane. The organic phase is washed with water, dried and concentrated by evaporation. The residue, recrystallized from dichloromethane-diisopropyl ether, yields 43 mg of 3-acetoxy-14α,17α-etheno-1,3,5(10)-estratriene- 16β,17β-diol. Melting point: 185° C. The mother liquor is chromatographed on 2 silica gel slabs, layer thickness of 1 mm, surface of 20×40 cm, mobile solvent: hexane-ethyl acetate (7:3). After the elution and recrystallization from dichloromethane-diethyl ether-pentane, 75 mg of 3,16β-diacetoxy-14α,17α-etheno-1,3,5(10)-estratrien- 17β-ol is obtained. Melting point: 202° C.

Example 8

14α,17α-Etheno-1,3,5(10)-estratriene-3,16β,17β-triol-triacetate

A solution of 370 mg of 14α,17α-etheno-1,3,5(10)-estratriene- 3,16β,17β-triol in a mixture of 3.7 ml of pyridine and 1.8 ml of acetic anhydride is mixed with 40 mg of 4-dimethylaminopyridine and allowed to stand for 18 hours at room temperature. The reaction product is precipitated by adding water and taken up in dichloromethane. The organic phase is washed with water, dried and concentrated by evaporation. The residue is chromatographed on 5 silica gel slabs, layer thickness of 1 mm, surface of 20×40 cm, mobile solvent hexane-ethyl acetate (7:3). After the elution and recrystallization from diethyl ether-pentane, 230 mg of 14α,17α-etheno-1,3,5(10)-estratriene-3,16β,17β-triol-triacetate is obtained. Melting point: 76° C.

Example 9

16β,17β-Diacetoxy-14α,17α-etheno-1,3,5(10)-estratrien-3-ol

A solution of 50 mg of 14α,17α-etheno-1,3,5(10)-estratriene- 3,16β,17β-triol-triacetate in 2.5 ml of methanol is heated to boiling with 0.4 ml of water and 100 mg of potassium carbonate for 24 hours. The reaction solution is then applied directly on 2 silica gel slabs, layer thickness of 1 mm and surface of 20×40 cm, and chromatographed with hexane-ethyl acetate (7:3). After elution and recrystallization from dichloromethane-hexane, 33 mg of 16β,17β-diacetoxy-14α,17α-etheno-1,3,5(10)-estratrien-3-ol results. Melting point: 214° C.

Example 10

14α,17α-Etheno-3,17β-dihydroxy-1,3,5(10)-estratrien-16-one

A solution of 150 mg of 3,16β,17β-triacetoxy-14α,17α-etheno-1,3,5(10)-estratriene-16α-carbonitrile in 15 ml of tetrahydrofuran is mixed under an argon atmosphere with 3 ml of K-Selectride$^{(R)}$ and the reaction mixture is stirred for 2 hours at room temperature. Following this, the reaction mixture is mixed with 30 ml of water and extracted several times with a dichloromethane-methanol mixture (9:1). The extracts are dried and concentrated by evaporation in a vacuum. The residue is chromatographed on 100 g of silica gel. By elution with a hexane-ethyl acetate gradient (0–40% of ethyl acetate), 50 mg, which is obtained in crystalline form from diethyl ether, is extracted.

Yield: 28 mg of 14α,17α-etheno-3,17β-dihydroxy- 1,3,5(10)-estratrien-16-one.

Melting point: greater than 300° C.

Example 11

14α,17α-Etheno-3,17β-dihydroxy-1,3,5(10)-estratrien-16-one

A solution of 384 mg of 3,16β,17β-triacetoxy-14α,17α-etheno-1,3,5(10)-estratriene-16α-carbonitrile in a mixture of 8 ml of dimethyl sulfoxide and 8 ml of tetrahydrofuran is mixed at 0° C. with 1.12 ml of 2N potassium hydroxide solution and maintained for 15 hours at 5° C. The reaction product is extracted with ethyl acetate, the extract is washed with water, dried and concentrated by evaporation in a vacuum. The residue, about 370 mg, is chromatographed on silica gel with hexane-ethyl acetate (1:1). Yield: 130 mg of 14α,17α-etheno-3,17β-dihydroxy-1,3,5(10)-estratrien-16-one. Melting point: greater than 300° C.

Example 12

14α,17α-Etheno-1,3,5(10)-estratriene-3,16β,17β-triol and 14α,17α-etheno-1,3,5(10)-estratriene-3,16α,17β-triol A solution of 120 mg of 14α,17α-etheno-3,17β-dihydroxy- 1,3,5(10)-estratrien-16-one in 15 ml of tetrahydrofuran is mixed with 100 mg of lithium alanate and stirred for 90 minutes at 20° C. The reaction mixture after adding 20 ml of aqueous saturated sodium fluoride solution is extracted with 150 ml of a dichloromethane-methanol mixture (7:3). The extract yields 30 mg of an oil after the concentration by evaporation. The aqueous phase is evaporated to dryness in a vacuum, the residue is mixed with 100 ml of methanol and heated briefly to boiling. After the filtering and evaporation of the solvent, 130 mg of a solid remains. The solid and the oil are chromatographed after the combining on a silica gel column (d= 4 cm, l= 20 cm) with 1 l of hexane-ethyl acetate (7:3). 20 mg of a mixture as well as 60 mg of 14α,17α-etheno-1,3,5(10)-estratriene-3,16β,17β-triol are isolated. The mixture is separated chromatographically on 4 silica gel slabs (20×20 cm, layer thickness of 0.25 mm) with hexane-ethyl acetate (7:3) as a mobile solvent, and 7 mg of 14α,17α-etheno-1,3,5(10)-estratriene- 3,16α,17β-triol is obtained.

Example 13

3,16β-Diacetoxy-14α,17α-ethano-1,3,5(10)-estratrien-17β-ol

A solution of 90 mg of 14α,17α-ethano-1,3,5(10)-estratriene- 3,16β,17β-triol in a mixture of 1.3 ml of pyridine and 0.7 ml of acetic anhydride is allowed to stand for 6 hours at room temperature. The reaction product is precipitated by adding water and taken up in dichloromethane. The organic phase is washed with water, dried and concentrated by evaporation. The residue, recrystallized from diethyl ether-pentane, yields 43 mg of 3,16β-diacetoxy-14α,17α-ethano-1,3,5(10)-estratrien-17β-ol. Melting point: 129.5° C.

Example 14

14α,17α-ethano-1,3,5(10)-estratriene-3,16β,17β-triol-triacetate

A solution of 250 mg of 14α,17α-ethano-1,3,5(10)-estratriene- 3,16β,17β-triol in a mixture of 3.7 ml of pyridine and 1.8 ml of acetic anhydride is mixed with 30 mg of 4-dimethylaminopyridine and allowed to stand for 15 hours at room temperature. The reaction product is precipitated by adding water and taken up in dichloromethane. The organic phase is washed with water, dried and concentrated by evaporation. The residue is chromatographed on a silica gel column (d= 4 cm, l= 20 cm) with one liter each of diethyl ether-pentane (6:4) and (1:1). After the recrystallization from diethyl ether-pentane, 108 mg of 14α,17α-ethano-1,3,5(10)-estratriene-3,16β,17β-triol-triacetate is obtained. Melting point: 122° C.

Example 15

3-Acetoxy-14α,17α-ethano-1,3,5(10)-estratriene-16β,17β-diol 180 mg of 3-acetoxy-14α,17α-etheno-1,3,5(10)-estratriene- 16β,17β-diol is dissolved in a mixture of 10 ml of ethanol and 4 ml of tetrahydrofuran. After adding 40 mg of palladium carbon catalyst (10% Pd), it is hydrogenated at 22° C. and a pressure of 1024 hPa. After absorption of 15.0 ml (calculated: 12.52 ml) of hydrogen within 10 minutes, it is suctioned off from the catalyst and the filtrate is evaporated to dryness and the residue is recrystallized from diethyl ether-hexane. 91 mg of 3-acetoxy-14α,17α-ethano- 1,3,5(10)-estratriene-16β,17β-diol is obtained. Melting point 191° C.

Example 16

14α,17α-Ethano-3,17β-dihydroxy-1,3,5(10)-estratrien-16-one 260 mg of 14α,17α-etheno-3,17β-dihydroxy-1,3,5(10)-estratrien- 16-one is dissolved in a mixture of 20 ml of ethanol and 10 ml of tetrahydrofuran. After addition of 30 mg of palladium-carbon catalyst (10% Pd) it is hydrogenated at 22° C. and a pressure of 1012 hPa. After absorption of 23.0 ml (calculated: 20.62 ml) of hydrogen within 15 minutes, it is suctioned off from the catalyst, the filtrate is evaporated to dryness and the residue is recrystallized from dichloromethane-methanol. 124 mg of 14α,17α-ethano-3,17β-dihydroxy-1,3,5(10)-estratrien-16-one is obtained. Melting point 259° C.

Example 17

14α,17α-ethano-1,3,5(10)-estratriene-3,16β,17β-triol and 14α,17α-ethano-1,3,5(10)-estratriene-3,16α,17β-triol A solution of 110 mg of 14α,17α-ethano-3,17β-dihydroxy- 1,3,5(10)-estratrien-16-one in 10 ml of tetrahydrofuran is mixed with 75 mg of lithium alanate and allowed to stand for 90 minutes at 20° C. After adding 10 ml of aqueous saturated sodium fluoride solution, the mixture is evaporated to dryness in a vacuum, the residue is mixed with 75 ml of methanol and heated to boiling, after the filtering, the solvent is evaporated. The remaining residue, chromatographed on a silica gel column with one liter of hexane-ethyl acetate (7:3) as an eluent, yields 53 mg of 14α,17α-ethano-1,3,5(10)-estratriene-3,16β,17β-triol, melting point: 228° C. (from diisopropyl ether-methanol) and 12 mg of 14α,17α-ethano-1,3,5(10)-estratriene-3,16α,17β-triol, melting point: 308° C. (from dichloromethane-methanol). Production of the initial compounds for variant B)

Example 18

3,16β,17β-Triacetoxy-14α,17α-etheno-estra-1,3,5(10)-triene- 16α-carbonitrile

A solution of 3.0 g of estra-1,3,5(10),14,16-pentaene-3,17-diol diacetate in 10 ml of dichloromethane is mixed with 10 ml of 1-cyanovinyl acetate and heated for 4 days in a closed tube to 140° C. The resinified reaction mixture is crushed in a mortar and treated with boiling acetone. After the decanting and evaporation of the solvent, 4.9 g of a residue, which is chromatographed on silica gel, remains. It is eluted with a hexane-ethyl acetate mixture (7:3) and 3.78 g is obtained which recrystallized from dichloromethane-hexane yields 3.28 g of 3,16β,17β-triacetoxy-14α,17α-etheno-estra-1,3,5(10)-triene-16α-carbonitrile. Melting point: 162° C.

Example 19

17β-Acetoxy-14α,17α-etheno-3-hydroxy-estra-1,3,5(10)-trien- 16-one and 14α,17α-etheno-3,17β-dihydroxy-estra-1,3,5(10)-trien- 16-one A solution of 385 mg of 16β,17β-diacetoxy-14α,17α-etheno- 3-methoxy-estra-1,3,5(10)-triene-16α-carbonitrile in a mixture of 8 ml of dimethyl sulfoxide and 8 ml of tetrahydrofuran is mixed at 0° C. with 1.2 ml of 2N potassium hydroxide solution and stored for 2 days at 0° C. The reaction mixture is mixed with water and extracted with ethyl acetate. The extract is washed with water, dried on sodium sulfate and concentrated by evaporation in a vacuum. The residue is chromatographed on silica gel. It is eluted with hexane-ethyl acetate mixtures (7:3 and 1:1) and recrystallized from pentane-diethyl ether. 84 mg of 17β-acetoxy-14α,17α-etheno-3-hydroxy-estra-1,3,5(10)-trien-16 -one with a melting point of 245° C. as well as 130 mg of 14α,17α-etheno-3,17β-dihydroxy-estra-1,3,5(10)-trien-16 -one, melting point 313° C., are obtained.

Example 20

14α,17α-Ethano-3,17β-dihydroxy-estra-1,3,5(10)-trien-16-one

A solution of 130 mg of 14α,17α-etheno-3,17β-dihydroxy-estra- 1,3,5(10)-trien-16-one in a mixture of 10 ml of tetrahydrofuran and 20 ml of ethanol is mixed with 30 mg of palladium carbon catalyst (10% Pd) and hydrogenated at 22° C. with hydrogen under atmospheric pressure. The catalyst is filtered off, the solvent is evaporated in a vacuum and the residue is crystallized from dichloromethane-methanol. 91 mg of 14α,17α-ethano-3,17β-dihydroxy-estra-1,3,5(10)-trien- 16-one with a melting point of 259° C. is obtained.

Example 21

14α,17α-Ethano-17β-hydroxy-3-methoxy-estra-1,3,5(10)-trien- 16-one

A solution of 500 mg of 14α,17α-etheno-17β-hydroxy-3 -methoxy-estra-1,3,5(10)-trien-16-one in a mixture of 25 ml of tetrahydrofuran and 25 ml of ethanol is mixed with 125 mg of palladium carbon catalyst (10% Pd) and hydrogenated at 25° C. with hydrogen under atmospheric pressure. The catalyst is filtered off, the solvent is evaporated in a vacuum and the residue is crystallized from hexane-ethyl acetate. 355 mg of 14α,17α-ethano-17β-hydroxy-3-methoxy-estra-1,3,5(10)-trien- 16-one is obtained.

Example 22 a) 20 ml of ammonia is condensed and 200 mg of sodium, cut into small sections, is added slowly, within 20 minutes. A deep blue solution is formed. 450 mg of 3,16β-17β-triacetoxy-14α,17α-etheno-estra-1,3,5(10)-triene-16α-carbonitrile, dissolved in 20 ml of tetrahydrofuran, is now instilled in the solution of metal sodium in liquid ammonia. The reaction mixture is stirred under dry ice cooling for 30 minutes. Then a saturated ammonium chloride solution is carefully added and the mixture is brought to room temperature. After the evaporation of the ammonia, it is mixed with water and extracted 6 times with 50 ml of dichloromethane-methanol (4:1). The combined extracts are dried on magnesium sulfate and concentrated by evaporation in a vacuum. The oily residue of 319 mg is chromatographed on a silica gel column. 260 mg is eluted with dichloromethane-methanol (9:1) which, recrystallized from dichloromethane-methanol, yields 125 mg of 14α,17α-etheno-estra- 1,3,5(10)-triene-3,16α,17β-triol with a melting point of 271° C.

b) A solution of 80 mg of 14α,17α-etheno-estra- 1,3,5(10)-triene-3,16α,17β-triol in a mixture of 8 ml of tetrahydrofuran and 2 ml of methanol is mixed with 80 mg of tris(triphenylphosphine)rhodium(I) chloride and shaken for 11 hours at 25° C. under hydrogen at atmospheric pressure. The solution is mixed with a little silica gel and concentrated by evaporation in a rotary evaporator. The residue is chromatographed on a silica gel column with hexane-ethyl acetate (4:6). 79 mg of a crystalline substance is eluted which, recrystallized from dichloromethane-methanol, yields 56 mg of 14α,17α-ethano-estra- 1,3,5(10)-triene-3,16α,17β-triol of melting point 312° C.

Example 23

15 ml of ammonia is condensed and 125 mg of sodium, cut into small sections, is added slowly, within 20 minutes. A deep blue solution is formed. 250 mg of 16β-17β-diacetoxy- 14α,17α-etheno-3-methoxy-estra-1,3,5(10)- triene-16α-carbonitrile, dissolved in 15 ml of tetrahydrofuran, is then instilled in the solution of metal sodium in liquid ammonia. The reaction mixture is stirred under dry ice cooling for 40 minutes. Then, a saturated ammonium chloride solution is carefully added and the mixture is brought to room temperature. After the evaporation of the ammonia, it is mixed with water and extracted with dichloromethane several times. The combined extracts are dried on sodium sulfate and concentrated by evaporation in a vacuum. The oily residue is chromatographed on silica gel. 165 mg is obtained which, recrystallized from hexane-ethyl acetate, yields 105 mg of 14α,17α-etheno-3-methoxy estra-1,3,5(10)-triene- 16α,17β-diol with a melting point of 193° C.

Example 24

10 ml of ammonia is condensed and a solution of 100 mg of 14α,17α-etheno-3,17β-dihydroxy-estra-1,3,5(10)-trien-16-one in 10 ml of tetrahydrofuran in instilled. This solution is mixed with 40 mg of sodium, cut into small sections, and stirred under dry ice cooling for 30 minutes. After this period, the originally deep blue solution is bleached. Then, a saturated ammonium chloride solution is added carefully and the mixture is brought to room temperature. After the evaporation of the ammonia, it is mixed with water and extracted several times with dichloromethane-methanol (4:1). The combined extracts are dried on sodium sulfate and concentrated by evaporation in a vacuum. The crystalline residue is recrystallized from dichloromethane-methanol. 62 mg of 14α,17α-etheno-estra-1,3,5(10)-triene- 3,16α,17β-triol with a melting point of 267° C. is obtained.

Example 25

20 ml of ammonia is condensed and a solution of 200 mg of 14α,17α-ethano-3,17β-dihydroxy-estra-1,3,5(10)-trien-16-one in 10 ml of tetrahydrofuran is instilled. The solution is mixed with 75 mg of sodium, cut into small sections, and stirred under dry ice cooling for 30 minutes. After this period, the originally deep blue solution is bleached. Then, a saturated ammonium chloride solution is carefully added and the mixture is brought to room temperature. After the evaporation of the ammonia, it is mixed with water and extracted several times with dichloromethane-methanol (4:1). The combined extracts are dried on sodium sulfate and concentrated by evaporation in a vacuum. The residue is recrystallized from dichloromethane-methanol. 120 mg of 14α,17α-ethano-estra-1,3,5(10)-triene-3,16α,17β-triol with a melting point of 314° C. is obtained.

Example 26

10 ml of ammonia is condensed and a solution of 50 mg of 14α,17α-ethano-17β-hydroxy-3-methoxy-estra-1,3,5(10)-trien- 16-one in 10 ml of tetrahydrofuran is instilled. This solution is mixed with 20 mg of sodium, cut into small sections, and stirred with dry ice cooling for 30 minutes. After this period, the originally deep blue solution is bleached. Then, a saturated ammonium chloride solution is carefully added and the mixture is brought to room temperature. After the evaporation of the ammonia, it is mixed with water and extracted several times with dichloromethane-methanol (4:1). The combined extracts are dried on sodium sulfate and concentrated by evaporation in a vacuum. The oily residue is chromatographed on silica gel. 47 mg is obtained which, recrystallized from dichloromethane-methanol, yields 22 mg of 14α,17α-ethano-3-methoxy-estra-1,3,5(10)-triene-16α,17β-diol with a melting point of 251° C.

Example 27

10 ml of ammonia is condensed and a solution of 150 mg of 14α,17α-etheno-17β-hydroxy-3-methoxy-estra-1,3,5(10)-trien- 16-one in 10 ml of tetrahydrofuran is instilled. This solution is mixed with 60 mg of sodium, cut into small sections, and stirred under dry ice cooling for 30 minutes. After this period, the originally deep blue solution is bleached. Then, a saturated ammonium chloride solution is carefully added and the mixture is brought to room temperature. After the evaporation of the ammonia, it is mixed with water and extracted several times with dichloromethane-methanol (4:1). The combined extracts are dried on sodium sulfate and concentrated by evaporation in a vacuum. The oily residue is chromatographed on silica gel. 116 mg is obtained which, recrystallized from hexane-ethyl acetate, yields 65 mg of 14α,17α-etheno-3-methoxy-estra-1,3,5(10)-triene-16α,17β-diol with a melting point of 195° C.

Example 28

10 ml of ammonia is condensed and a solution of 50 mg of 17β-acetoxy-14α,17α-etheno-3-hydroxy-estra-1,3,5(10)-trien- 16-one in 10 ml of tetrahydrofuran is instilled. This solution is mixed with 20 mg of sodium, cut into small sections, and stirred with dry ice cooling for 30 minutes. After this period, the originally deep blue solution is bleached. Then, a saturated ammonium chloride solution is carefully added and the mixture is brought to room temperature. After the evaporation of the ammonia, it is mixed with water and extracted several times with dichloromethane-methanol (4:1). The combined extracts are dried on sodium sulfate and concentrated by evaporation in a vacuum. 43 mg of a crystalline residue is obtained, which recrystallized from dichloromethane-methanol, yields 31 mg of 14α,17α-etheno-estra-1,3,5(10)-triene-3,16α,17β-triol with a melting point of 267° C.

Example 29

20 ml of ammonia is condensed and a solution of 250 mg of 17β-acetoxy-14α,17α-ethano-3-methoxy-estra-1,3,5(10)-trien- 16-one in 20 ml of tetrahydrofuran is instilled. This solution is mixed with 100 mg of sodium, cut into small sections, and stirred with dry ice cooling for 30 minutes. After this period, the originally deep blue solution is bleached. Then, a saturated ammonium chloride solution is carefully added and the mixture is brought to room temperature. After the evaporation of the ammonia, it is mixed with water and extracted several times with dichloromethane. The combined extracts are dried on sodium sulfate and concentrated by evaporation in a vacuum. The residue, recrystallized from hexane-ethyl acetate, yields 165 mg of 14α,17α-ethano-3-methoxy-estra-1,3,5(10)-triene-16α,17β-diol with a melting point of 248° C.

Example 30

17β-acetoxy-3-benzyloxy-14α,17α-etheno-1,3,5(10)-estratriene- 16α-carbaldehyde (30)

19.44 g of 3-benzyloxy-1,3,5(10)14,16-estra-pentaen-17-yl acetate (melting point 114°–115° C.; produced from 3-benzyloxy-estrone analogously to the series of reactions according to J. Pataki et al., J. Org. Chem. 37 2127 (1972)) and 13.2 ml of acrolein in 205 ml of toluene are mixed by drops with ice cooling with 0.6 ml of boron trifluoride etherate in 20 ml of toluene under nitrogen. The reaction mixture is stirred for 16 hours at room temperature and then added on ice/water. Then, it is extracted with ethyl acetate, the organic phase is washed neutral with water and dried on sodium sulfate. Filtration and evaporation of the solvent yield 24.2 g of solid residue. By recrystallization in ethyl acetate, 16.7 g of 30 of melting point 150°–151° C. is obtained.

Example 31

3-benzyloxy-17-oxo-1,3,5(10)-estratraene-14β-propionic acid aldehyde (31)

16.7 g of 30 in 556 ml of tetrahydrofuran and 139 ml of methanol are mixed with 382 ml of 0.1N lithium hydroxide solution and stirred for 18 hours at room temperature. The reaction mixture is acidified with 45 ml of 1N hydrochloric acid and then the tetrahydrofuran is evaporated. The aqueous phase is extracted with ethyl acetate, the organic phase is washed neutral with water and dried on sodium sulfate; filtration and evaporation of the solvent yield 17 g of oil as a residue. By chromatography on silica gel with ethyl acetate/hexane (1:2), 5.65 g of 31 is obtained as a foamy solid.

Example 32

14β-[(E/Z)-3-acetoxy-2-propenyl]-3-benzyloxy-1,3, 5(10),15 -estratetraen-17-one (32)

5.6 g of 31, 101.6 ml of isopropenyl acetate and 1.09 g of p-toluenesulfonic acid are refluxed for 6 hours under nitrogen. The reaction mixture is diluted with ethyl acetate, the organic phase is washed with sodium bicarbonate solution and water and dried on sodium sulfate. Filtration and evaporation of the solvent yield 6.7 g of 32 as an oily residue, which is subjected to Lemieux-Johnson oxidation without further purification.

Example 33

3-benzyloxy-17-oxo-1,3,5(10),15-estratetraen-14β-acetic aldehyde (33)

6.6 g of 32 in 117 ml of tetrahydrofuran is mixed at room temperature with 295 mg of osmium tetroxide in 59 ml of tetrahydrofuran and after 5 minutes with 59 ml of water. After another 5 minutes, 17.7 g of sodium periodate is added with ice cooling and stirred for 4 hours at room temperature. The reaction mixture is stirred in common salt solution and extracted with ethyl acetate. The organic phase is washed with water and dried on sodium sulfate. After filtration, evaporation of the solvent and filtration of the foamy residue by silica gel with ethyl acetate/hexane (1:2), 2.53 g of 33 is obtained as a colorless oil after concentration by evaporation.

Example 34

3-benzyloxy-17-oxo-1,3,5(10)-estratriene-14β-acetic aldehyde (34)

2.23 g of 33 in 56 ml of tetrahydrofuran is hydrogenated with 0.45 g of Pd-BaSO$_4$ (10%) at standard pressure. After removal of the catalyst and concentration by evaporation of the filtrate, 2.48 g of oil is obtained. Chromatography on silica gel with ethyl acetate/hexane (1:2) yields 1.8 g of 34 as a colorless oil.

Example 35

3-benzyloxy-14α,17α-ethano-1,3,5(10)-estratriene-16α, 17β-diol (35)

1.75 g of 34 in 29 ml of tetrahydrofuran is mixed by drops under nitrogen at −10° C. with 8.7 ml of a 1 molar solution of titanium(IV) chloride in methylene chloride. After 10 minutes, 850 mg of zinc is added in portions within 40 minutes. Then, it is stirred for another hour with ice cooling and then the reaction mixture is poured into ice-cooled potassium carbonate solution. After dilution with methylene chloride, it is separated from the sludge, the organic phase is washed neutral with water and dried on sodium sulfate. After filtration and evaporation of the solvent, 1.35 g of oil is obtained. Chromatography on silica gel with ethyl acetate/hexane (1:1) yields 270 mg of 35 of melting point 186° C.

Example 36

14α,17α-Ethano-1,3,5(10)-estratriene-3,16α,17β-triol (36)

260 mg of 35 in 50 ml of ethanol is hydrogenated with 65 mg of Pd-C (10%) at standard pressure. After removal of the catalyst and concentration of the filtrate by evaporation, 60 mg of solid is obtained. Chromatography on silica gel with ethyl acetate/hexane (3:1) yields 23 mg of 36 of melting point 310°–312° C.

Example 37

17β-Acetoxy-14α,17α-ethano-3-methoxy-1,3,5(10)-estratriene- 16α-carbaldehyde (37)

10.0 g (30.8 mmol) of 3-methoxy-1,3,5(10),14,16-estrapentaen- 17-yl-acetate [G. M. Rasmusson et al, Steroids 22, 107 (1973)] and 4.17 ml (62.7 mmol) of acrolein in 124 ml of toluene is mixed by drops under ice cooling with 0.19 ml (1.6 mmol) of boron trifluoride etherate in 11.4 ml of toluene. The reaction mixture is stirred for 16 hours at room temperature and then added to ice/water. Then, it is extracted with ethyl acetate and the organic phase is dried after the washing with sodium bicarbonate solution and water on sodium sulfate. Filtration and evaporation of the solvent yield 9.8 g of solid residue. By chromatography on silica gel with ethyl acetate/hexane (1:2→1:1), 8.55 g of (37) of melting point 183°–185° C. is obtained. $[\alpha]_D^{20}$+ 102.5° (C O,120, CHCl$_3$)

Example 38

17β-Acetoxy-14α,17α-ethano-3-methoxy-1,3,5(10)-estratriene- 16α-carbaldehyde (38)

2.0 g of (37) in 250 ml of ethyl acetate is hydrogenated with 0.5 g of Pd-C (10%) at standard pressure. After removal of the catalyst and evaporation of the solvent, 1.99 g of (38) of melting point 151°–152° C. is obtained.

Example 39

17β-Acetoxy-16-acetoxymethylene-14α,17α-ethano-3-methoxy- 1,3,5(10)-estratriene (39)

A solution of 29.1 g of 17β-acetoxy-14α,17α-ethano-3 -methoxy-1,3,5(10)-estratriene-16α-carbaldehyde (38) in 130 ml of acetic anhydride and 130 ml of isopropenyl acetate is gently refluxed (bath temperature 120° C.) for 31 hours after adding 10.73 g of p-toluenesulfonic acid. After the cooling off, the reaction solution is slowly instilled in about 3 l of ice-cold 5% NaHCO$_3$ solution, stirred for 60 minutes at room temperature and extracted with ethyl acetate. The ethyl acetate extracts are dried on Na$_2$SO$_4$ and concentrated by evaporation. After chromatography of the crude product on about 1.5 kg of silica gel with hexane/ethyl acetate, 30.0 g of enol acetate 39 is obtained as a colorless oil, which thoroughly crystallizes when left standing for a prolonged period.

$^1$H-NMR (CDCl$_3$, 300 MHz): δ=0.90 ppm (s,3H,H-18): 2.11(s, 3H,COCH$_3$): 2,15 (s,3H,COCH$_3$): 3.78 (s,3H, OCH$_3$): 6.64 (m, 1H,H-4): 6.72 (m,1H,H-2): 7.11 (m,1H, enol acetate-H): 7.21 (d,I=9Hz,1H,H-1).

Example 39a

17β-Acetoxy-14β,17β-ethano-16β-hydroxymethyl-3-methoxy-estra- 1,3,5(10)-triene

To a solution of 63.0 g Cerium-(III)-chloride-heptahydrate in 1096 ml of methanol cooled with ice water a solution of 87.1 g 17β-acetoxy-14α,17α-ethano-3-methoxy-estra- 1,3,5(10)-triene-16α-carbaldehyde in 1218 ml of tetrahydrofurane and of 957 ml methanol is added dropwise. After having added 8.45 g sodium borohydride in single portions the reaction mixture is stirred for 16 h at room temperature. The reaction mixture is poured into 5 l of water and the aqueous phase extracted with dichloromethane. After drying (Na$_2$SO$_4$) and concentrating, 86.5 g of the title compound are obtained as colorless oil. $^1$H-NMR(CDCl$_3$); δ=1.02 ppm (s,3H,H-18); 2.07 (s,3H,OAc); 3.52–3.65 and 3.83–3.94 (m,2H,CH$_2$OH) ); 3.78 (s,3H,OCH$_3$); 6.62 (d,1H, H-4); 6.71 (dd,1H,H-2); 7.21 (d,1H,H-1).

Example 40

17β-Acetoxy-14α,17α-ethano-3-methoxy-1,3,5(10)-estratrien- 16-one (40)

A solution of 30.0 g of enol acetate 39 in 900 ml of dichloromethane and 450 ml of methanol is cooled to –70° C. Under vigorous stirring, an ozone-oxygen stream is directed through the solution. The O$_2$/O$_3$ mixture is produced by establishing an O$_2$ flow of 301/h on the ozonizer (ozone generator OZ II, Fischer-Labortechnik, Bad Godesberg); the O$_3$ concentration of the primary stream is decreased after leaving the ozonizer by admixing oxygen one more time by a factor of 2–3. After passing in the O$_2$/O$_3$ mixture thus produced for about 2 hours, the reaction solution is flushed with nitrogen and then 20.7 g of triphenylphosphine is added by portions within 15 minutes. After the addition, it is stirred for another 30 minutes at –70° C., it is allowed to come to room temperature and the reaction solution is poured in an about 3 l NaHCO$_3$ solution. The CH$_2$-Cl$_2$ phase is separated, dried on Na$_2$SO$_4$ and concentrated by evaporation. After chromatography on silica gel with hexane/ethyl acetate and recrystallization of the main product from ethyl acetate diisopropyl ether, 17.2 g of 40 of melting point 216°–218° C. is obtained.

Example 40a

17β-Acetoxy-14α,17α-ethano-3-methoxy-16α-(4 -toluenesulfonyloxy)-methyl-estra-1,3,5(10)-triene A solution of 172.8 g 17β-acetoxy-14α,17α-ethano-16α-hydroxymethyl-3-methoxy-estra-1,3,5(10)-triene in 1800 ml of pyridine is treated—under cooling with ice water—in portions with 171.4 g 4-toluenesulfonylchloride. After addition, the reaction mixture is stirred for 2.5 h at room temperature, then the reaction solution poured into 5 l of water and thereto added 75 g of NaHCO$_3$ in portions. After stirring for 30 minutes at room temperature the solution is extracted with ethyl acetate. The ethyl acetate-extracts are washed with water and 2n.HCl, dried over Na$_2$SO$_4$ and concentrated. The obtained crude product of the title compound (245.8 g) is used without further purification for the following reaction step.

Example 41

14α,17α-Ethano-3-methoxy-1,3,5(10)-estratriene-16β,17β-diol (41)

A solution of 500 mg of sodium borohydride in 100 ml of 80% aqueous ethanol is instilled with ice water cooling in a solution of 2.3 g of ketone 40 in 160 ml of ethanol. Then, it is stirred for 14 hours at room temperature, then poured into about 1 l of water and extracted with ethyl acetate. After recrystallization of the crude product from ethyl acetate diisopropyl ether, 2.05 g of 41 of melting point 170°–172° C. is obtained. [α]$_D^{20}$+ 48.8° (CHCl$_3$, c=0,510)

Example 41a

3-Methoxy-14β-(2-propenyl)-estra-1,3,5(10)-triene-17-one

A solution of 245.8 g of the crude product obtained according to Example 40a in 2400 ml of methanol and 964 ml of 2n-NaOH is stirred for 2.5 h at 60° C. After cooling the reaction mixture is poured into 5 l of water and extracted with dichloromethane. The dichloromethane-extracts are washed with water, dried over Na$_2$SO$_4$/carbon and concentrated. The oily residue is dissolved in 150 ml of methanol and 15 ml of ethyl acetate under warming and thereafter crystallized at room temperature. After filtration 164.8 g of the title compound, melting point 75°–77° C., are obtained. Chromatography of the mother liquor over silica gel with hexane/ethyl acetate yields further 19 g of the product $^1$H-NMR (CDCl$_3$); δ= 1.11 ppm (s,3H,H-18); 3.78 (s,3H, OHCH$_3$); 5.00–5.14 (m,2h,CH=CH$_2$), 5.70–5.85 (m,1H, CH=CH$_2$).

Example 42

3-Methoxy-17-oxo-1,3,5(10)-estratriene-14β-acetic aldehyde (42)

A solution of 1.9 g of diol 41 in 23 ml of dichloromethane and 23 ml of isopropanol is mixed with ice water cooling in portions with 2.01 g of H$_5$IO$_6$. It is stirred for 15 minutes at 25° C., poured in water and extracted with dichloromethane. The CH$_2$Cl$_2$ extracts are washed with 5% aqueous NaHSO$_3$, dried on Na$_2$SO$_4$ and concentrated by evaporation. After crystallization of the crude product from ethyl acetate/ diisopropyl ether, 1.74 g of 42 of melting point 126°–128° C. is obtained.

Example 42a

3-Methoxy-17-oxo-estra-1,3,5(10)-triene-14β-acetaldehyde

A solution of 25 g of 3-methoxy-14β-(2-propenyl)-estra-1,3,5(10)-triene-17-one in 750 ml of dichloromethane and of 375 ml of methanol is cooled to –70° C. Under vigorous stirring a stream of ozone/oxygen (O$_2$ stream rate 80 l/h production rate of O$_3$ 10 g/h) is passed through the solution. After 50 minutes the reaction mixture is rinsed with nitrogen, 17.33 g of triphenyl phosphine is added in portions, stirred for further 30 minutes at –70° C. and allowed to warm up to room temperature. For working up the reaction mixture is poured into NaHCO$_3$-solution and extracted with dichloromethane. After chromatography over silica gel with hexane/ethyl acetate and crystallization from ethyl acetate/ diisopropyl ether 21.6 g of the title compound, melting point 216°–218° C., are obtained.

Example 43

14α,17α-Ethano-3-methoxy-1,3,5(10)-estratriene-16α,17β-diol (43)

2.5 ml of a 1M solution of titanium tetrachloride in dichloromethane is instilled at −10° C. in a solution of 500 mg of aldehyde 42 in 9 ml of dichloromethane. Then, 242 mg of zinc powder is added within 40 minutes and stirred for 60 minutes at 0° C. For working up, the reaction solution is poured in ice-cold $K_2CO_3$ solution, the resulting suspension is filtered on Celite and the resulting filtration residue is washed with $CH_2Cl_2$. The $CH_2Cl_2$ phase is washed with water, dried ($Na_2SO_4$) and concentrated by evaporation. Chromatography on silica gel with hexane/ethyl acetate yields 320 mg of crystalline 43; $^1$H-NMR (pyridine-$d_5$, 300 MHz); δ= 1.15 ppm (s,3H,H-18); 3.73 (s,3H,$OCH_3$); 4.78 (m,1H,H-16).

Example 44

16α,17β-Diacetoxy-14α,17α-ethano-3-methoxy-1,3,5(10)-estratriene (44)

0.68 ml of acetyl chloride is instilled with ice water cooling in a suspension of 310 mg of diol 43 and 1.42 g of sodium iodide in 20 ml of acetonitrile and stirred for 30 minutes at +5° to +10° C. Then, it is poured in $NaHSO_3$ solution and extracted with ethyl acetate. After crystallization of the crude product from ethyl acetate/diisopropyl ether, 270 mg of 44 of melting point 170°–172° C. is obtained.

Example 45

3,16α,17β-Triacetoxy-14α,17α-ethano-1,3,5(10)-estratriene (45)

A suspension of 49 mg of diacetate 44 and 178 mg of sodium iodide in 3 ml of acetonitrile is refluxed for 3 hours after adding 0.15 ml of trimethylchlorosilane. After cooling, it is poured in $NaHSO_3$ solution and extracted with ethyl acetate. The crude product obtained after the concentration by evaporation is stirred in 1 ml of acetic anhydride and 0.5 ml of pyridine for 30 minutes at 60° C. The reaction solution is instilled in saturated $NaHCO_3$ solution and extracted with ethyl acetate. After chromatography on silica gel, 29 mg of 45 of melting point 159°–161° C. is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 14α,17α-bridged estratriene of formula I

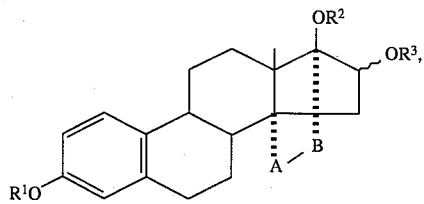

wherein (a) $OR^3$ is in α-position $R^1$ is (i) hydrogen, (ii)

in which $R^4$ is an organic radical with up to 11 carbon atoms (iii) $-(CH_2)_n COOH$ wherein n= 1–4, or (iv) benzyl, $C_1$–$C_8$ alkyl or $C_3$–$C_5$ cycloalkyl, $R^2$ and $R^3$ are each independently (i) hydrogen, (ii)

in which $R^4$ is an organic radical with up to 11 carbon atoms, or (iii) $-(CH_2)_n COOH$ wherein n=1–4, or (b) $OR^3$ is in β-position $R^1$ is (i) hydrogen, (ii) an acyl group with 1 to 12 carbon atoms or (iii) $C_1$–$C_8$ alkyl, $R^2$ and $R^3$ are each independently (i) hydrogen or (ii) an acyl group with 1 to 12 carbon atoms, and both in (a) and (b) A—B is an etheno or ethano bridge.

2. A 14α,17α-bridged estratriene of claim 1, wherein $R^1$, $R^2$ and $R^3$ in (b) (ii) are each independently a radical of a $C_{1-12}$-carboxylic acid.

3. A 14α,17α-bridged estratriene of claim 2, wherein the carboxylic acid is (a) an aliphatic, cycloaliphatic, aliphatic-cycloaliphatic or cycloaliphatic-aliphatic carboxylic acid in which the cycloaliphatic portions have 3–7 carbon atoms and the aliphatic and cycloaliphatic portions may contain 1–2 unsaturations, (b) a $C_{5-12}$-aromatic carboxylic acid, or (c) a $C_{2-6}$-dicarboxylic acid.

4. A 14α,17α-bridged estratriene according to claim 2, wherein $R^1$, $R^2$ and/or $R^3$ have 2 to 8 carbon atoms.

5. A 14α,17α-bridged estratriene according to claim 2, wherein $R^1$, $R^2$ and $R^3$ are identical and have 2 to 8 carbon atoms.

6. A 14α,17α-bridged estratriene according to claim 2, wherein $R^1$ and $R^3$ are identical and have 2 to 8 carbon atoms and $R^2$ is a hydrogen atom or is other than $R^1$ and $R^3$ and has 2 to 8 carbon atoms.

7. A 14α,17α-bridged estratriene according to claim 2, wherein $R^2$ and $R^3$ are identical and have 2 to 8 carbon atoms, and $R^1$ is a hydrogen or is other than $R^2$ and $R^3$ and has 2 to 8 carbon atoms.

8. A 14α,17α-bridged estratriene according to claim 2, wherein $R^2$ and $R^3$ are hydrogen and $R^1$ has 2 to 8 carbon atoms.

9. A 14α,17α-bridged estratriene according to claim 2, wherein $R^1$ is a methyl group and $R^2$ and $R^3$ are hydrogen or $R^2$ and $R^3$ are an acyl group with 2 to 8 carbon atoms, and then $R^2$ and $R^3$ are identical.

10. A 14α,17α-bridged estratriene of claim 1, wherein $R^4$ is alkyl, alkenyl, dialkenyl, cycloalkyl, cycloalkenyl, alkyl-cycloalkyl, cycloalkyl-alkyl or $C_{5-11}$-aromatic in which any cycloalkyl portions present have 3–7 carbon atoms.

11. A 14α,17α-bridged estratriene of formula I according to claim 1, wherein $OR^3$ is in the α-position and A—B is an etheno bridge.

12. A 14α,17α-bridged estratriene of formula I according to claim 1, wherein $OR^3$ is in the α-position and A—B is an ethano bridge.

13. A 14α,17α-bridged estratriene of formula I according to claim 1, wherein $OR^3$ is in the β-position and A—B is an etheno bridge.

14. A 14α,17α-bridged estratriene of formula I according to claim 1, wherein $OR^3$ is in the β-position and A—B is an ethano bridge.

15. A compound of claim 1, selected from the group consisting of 14α,17α-ethano-1,3,5(10)-estratriene- 3,16α, 17β-triol;

14α,17α-ethano-3-methoxy-1,3,5(10)-estratriene-16β, 17β-diol;
14α,17α-ethano-3-methoxy-1,3,5(10)-estratriene-16α,17β-diol;
14α,17α-ethano-1,3,5(10)-estratriene-3,16β,17β-triol;
3-acetoxy-14α,17α-etheno-1,3,5(10)-estratriene-16β,17β-diol;
3,16β-diacetoxy-14α,17α-etheno-1,3,5(10)-estratriene-17β-ol;
14α,17α-etheno-1,3,5(10)-estratriene-3,16β,17β-triol-triacetate;
16β,17β-diacetoxy-14α,17α-etheno-1,3,5(10)-estratrien-3-ol;
14α,17α-etheno-1,3,5(10)-estratriene-3,16β,17β-triol;
14α,17α-etheno-1,3,5(10)-estratriene-3,16α,17β-triol;
3,16β-diacetoxy-14α,17α-ethano-1,3,5(10)-estratrien-17β-ol;
14α,17α-ethano-1,3,5(10)-estratriene-3,16β,17β-triol-triacetate;
3-acetoxy-14α,17α-ethano-1,3,5(10)-estratriene-16β,17β-diol;
14α,17α-ethano-1,3,5(10)-estratriene-3,16β,17β-triol;
14α,17α-ethano-1,3,5(10)-estratriene-3,16α,17β-triol;
3-benzyloxy-14α,17α-ethano-1,3,5(10)-estratriene-16α, 17β-diol;
14α,17α-ethano-1,3,5(10)-estratriene-3,16α,17β-triol;
14α,17α-ethano-3-methoxy-1,3,5(10)-estratriene-16α,17β-diol;
16α,17β-diacetoxy-14α,17α-ethano-3-methoxy-1,3,5(10)-estratriene; and
3,16α,17β-triacetoxy-14α,17α-ethano-1,3,5(10)-estratriene.

16. A pharmaceutical composition, comprising a compound of claim 1 and a pharmaceutically acceptable carrier.

17. A method of treating estrogen deficiency, comprising administering an effective amount of a compound of claim 1.

18. A method of treating amenorrhea, dysmenorrhea, sterility, endometritis, colpitis, menopausal symptoms, or osteoporosis, comprising administering an effective amount of a compound of claim 1.

19. A method for achieving a contraceptive effect in a female, comprising administering an effective amount of a compound of claim 1.

* * * * *